(12) United States Patent
Wegand et al.

(10) Patent No.: US 7,000,451 B1
(45) Date of Patent: Feb. 21, 2006

(54) FRICTION TESTING DEVICE

(76) Inventors: John C. Wegand, 3405 Elsa Ave., Waldorf, MD (US) 20603; David E. Palaith, 124 Severn Way, Arnold, MD (US) 21012; Keith E. Lucas, 15901 Croom Airport Rd., Upper Marlboro, MD (US) 20773

( * ) Notice: Subject to any disclaimer, the term of this patent is extended or adjusted under 35 U.S.C. 154(b) by 80 days.

(21) Appl. No.: 10/714,743

(22) Filed: Nov. 17, 2003

(51) Int. Cl.
*G01N 19/02* (2006.01)
*G01B 21/30* (2006.01)

(52) U.S. Cl. ............................. 73/9; 73/105
(58) Field of Classification Search ............... 73/9–10, 73/105
See application file for complete search history.

(56) References Cited

U.S. PATENT DOCUMENTS

| | | | |
|---|---|---|---|
| 3,724,259 A | 4/1973 | Blakeley et al. | |
| 3,975,940 A | 8/1976 | Brungraber | |
| 4,315,425 A | 2/1982 | Zbornik et al. | |
| 4,498,329 A * | 2/1985 | Bloomer et al. | 73/9 |
| 4,569,222 A | 2/1986 | Arnold et al. | |
| 4,594,878 A | 6/1986 | Abe et al. | |
| 4,712,418 A | 12/1987 | Augustin | |
| 4,759,209 A | 7/1988 | Brungraber | |
| 4,895,015 A | 1/1990 | English | |
| 5,259,236 A | 11/1993 | English | |
| 5,756,886 A * | 5/1998 | Nishimura et al. | 73/105 |
| 5,795,990 A | 8/1998 | Gitis et al. | |
| 5,900,531 A | 5/1999 | Mani et al. | |
| 6,612,151 B1 * | 9/2003 | Haines | 73/9 |
| 6,857,306 B1 * | 2/2005 | Domeier | 73/10 |

FOREIGN PATENT DOCUMENTS

JP 2001108608 A * 4/2001

* cited by examiner

Primary Examiner—Thomas P. Noland

(57) ABSTRACT

A device for the determination of the frictional characteristics of large surfaces comprising: a frame; a drive motor mounted atop the frame; a drive train; a horizontal measurement arm attached to the drive train and capable of circular rotation; a spherical frictional slider attached to the distal end of the measurement arm that contacts and slides along a surface under evaluation; the frictional slider comprising a spherical member that directly engages the surface under evaluation; and a tangential force detector on the measurement arm to measure the resistance encountered by the spherical member as it slides along the surface under evaluation.

15 Claims, 2 Drawing Sheets

FRICTION TESTING DEVICE

FIELD OF THE INVENTION

The present invention relates to devices for determining the friction characteristics of surfaces, and more particularly to such a device for the determination of the frictional characteristics of large surfaces such as floor, landing areas and the like.

BACKGROUND OF THE INVENTION

The determination of the frictional characteristics of surfaces has long been and remains critical in many areas of industry, the military etc. A particularly important application of such devices is in the determination of the frictional characteristics of surfaces aboard ships where the movement of personnel over surfaces that may be wet under less than ideal conditions is extremely important and may be the determinant factor in the safety of military personnel.

As will be apparent to those skilled in the arts related to the determination of the frictional characteristics of surfaces, a large number of devices and a great deal of effort has been devoted to the development of improved such devices and no extended discussion of such efforts and the resultant devices is required here. Suffice it to say that numerous such devices have been designed, manufactured and applied to obtain accurate measurements of the frictional characteristics of large surfaces.

In spite of these efforts, there remains a need for further improved such devices, especially as they apply to the aforementioned shipboard surfaces under less than ideal conditions as are routinely encountered by military personnel aboard ships, especially on the decks of, for example, aircraft carriers.

OBJECT OF THE INVENTION

It is therefore an object of the present invention to provide an improved device for the determination of the frictional characteristics of large surfaces.

SUMMARY OF THE INVENTION

According to the present invention, there is provided a device for the determination of the frictional characteristics of large surfaces comprising: a frame; a drive train; a horizontal measurement arm attached to the rotary motion transfer mechanism and capable of circular rotation; a spherical frictional slider attached to the distal end of the measurement arm that contacts and slides along a surface under evaluation; the spherical frictional slider comprising a spherical member that directly engages the surface under evaluation; and a tangential force detector on the measurement arm to measure the resistance encountered by the spherical frictional slider as it slides along the surface under evaluation. According to various alternative preferred embodiments, the system further includes an angular motion detector to determine the relative angular position of the measurement arm, a vertical deviation detector to measure changes in the topography of the surface under evaluation and a lift mechanism to raise and lower the frictional slider into and out of contact with the surface under evaluation.

DETAILED DESCRIPTION

Figure 1:
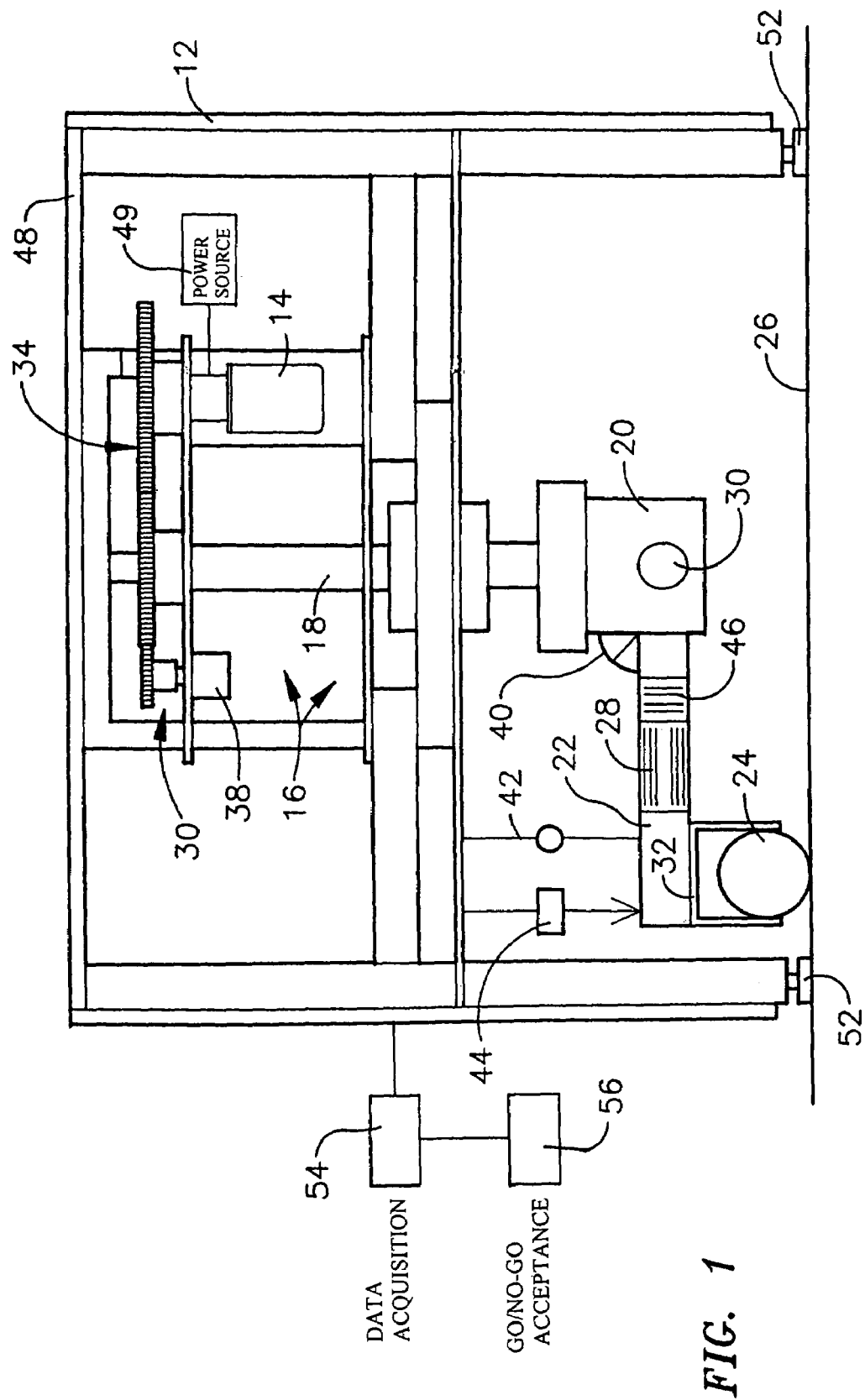
FIG. 1 is a side view of the friction testing device of the present invention.

Referring now to FIG. 1 that depicts a side view of the friction testing device of the present invention, the friction testing device 10 of the present invention comprises a frame 12, a drive motor 14 mounted in said frame, a mechanism 16 for transferring motion produced by motor 14 to a measurement arm 22, mechanism 16 is identified as the drive train hereinafter and comprises a mechanism 24 for transferring motion produced by motor 14 to a drive shaft 18, and a mechanism 20 for transferring the motion from drive shaft 18 to measurement arm 22, at the distal end of measurement arm 22, a spherical frictional slider 24 that contacts a surface 26 that is under frictional evaluation; and a tangential force detector 28 mounted on said measurement arm.

Figure 2:
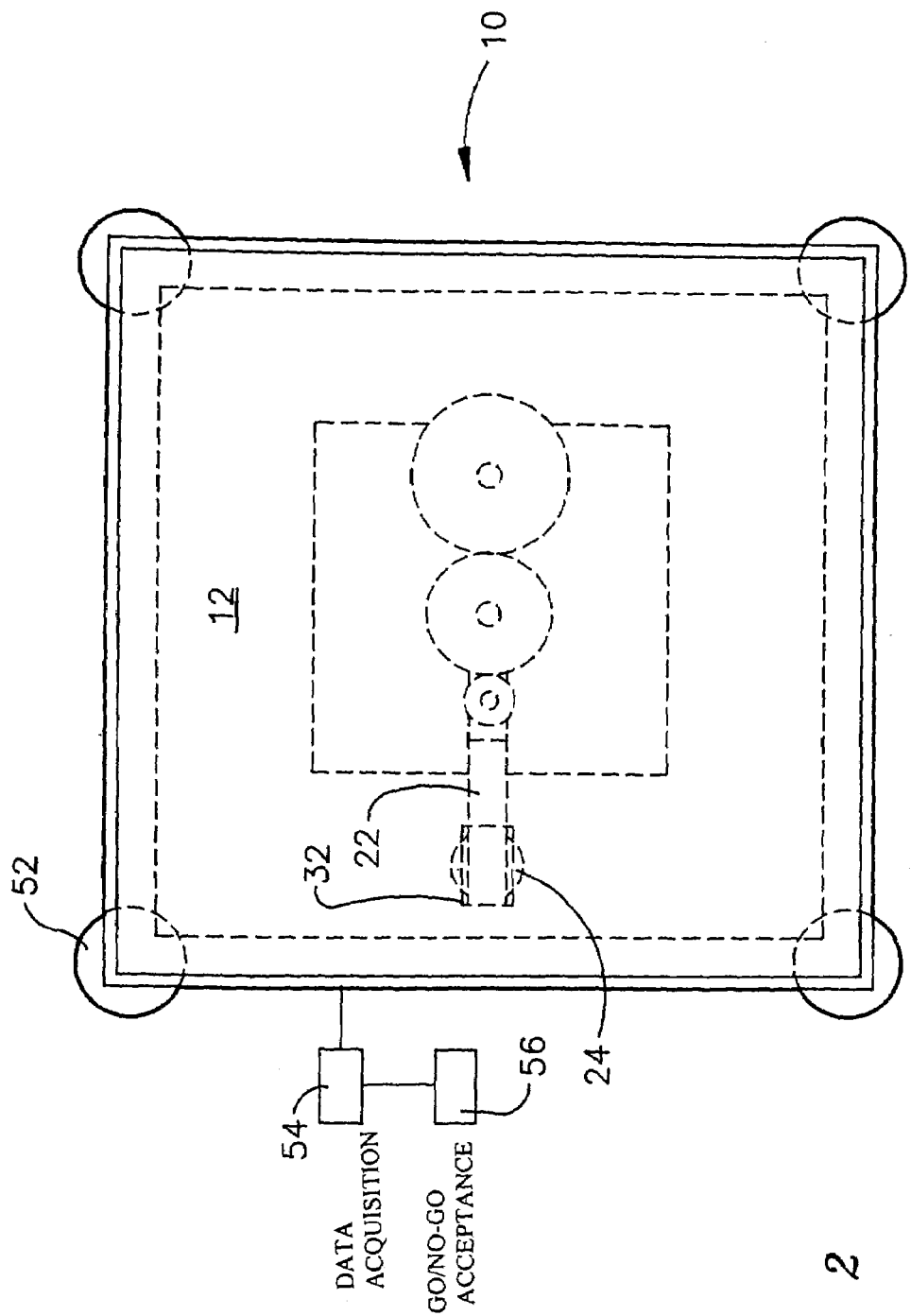
FIG. 2 is a top plan view of the friction testing device of the present invention.

Frame 12 is, of course provides support for motor 14 and may, according to various alternative preferred embodiments described below, incorporate additional handling enhancement and protective members. Motor 14 may be of any design or derive power from any suitable source such as an AC or DC electrical power source 49 or even a gasoline engine capable of delivering a consistent and reliable source of rotary motion. Drive train 16 may also be of any of a variety of designs and configurations so long as it is capable of delivering reliable and consistent rotary motion to measurement arm 22. In the embodiment depicted in FIGS. 1 and 2, drive train 16 comprises a gear assembly 34 that transfers rotary motion from motor 14 to drive shaft 18 and a yoke and bearing assembly 20 that transfers rotary motion from drive shaft 18 to measurement arm 22. The bearing assembly allows for appropriate rotary engagement of drive shaft 18 with measurement arm 22 while yoke 30 allows measurement arm 22 to float over or be pressed against surface 26. At the distal end of measurement arm 22 is spherical frictional slider 24. In the embodiment depicted in the accompanying Figures, spherical frictional slider 24 is ball shaped and frictionally or otherwise, i.e. with screws, bolts or other securing devices, secured in a holder 32 that limits the ability of spherical frictional slider 24 to rotate as it slides across surface 26. The use of holder 32 allows spherical frictional slider 24 to be adjusted or replaced easily in the field without the use of tools so that, for example, a non-used/non-worn area on spherical frictional slider 24 can be brought into contact with surface 26 for multiple or repetitive testing.

Measurement arm 22 is capable of nearly 360° travel in a circular path along surface 26. According to the embodiment depicted in the Figures, after travel in a first direction, because of the design of gear assembly 34, measurement arm 22 reverses direction and returns to its starting position. Using such a circular path minimizes dependence of the coefficient of friction on any directional or anisotropic properties of surface 26.

Measurement arm 22 may be fabricated from any suitable material such as a thin metallic strip or polymeric strip that can undergo limited bending under the load conditions anticipated in the course of any frictional measurement. Thus, tangential force detector 28 is incorporated into measurement arm 22 to measure the frictional force caused by spherical friction slider 24 traversing surface 26 as manifested by limited bending of measurement arm 22. One such suitable tangential force detector 28, and that depicted in the Figures, comprises one or an array of strain gauges mounted on the surface of measurement arm 22 parallel to the normal plane of surface 26 to form a Wheatstone bridge.

As is well known to the practioners of the tribological arts, the coefficient of friction or COF is not an absolute value, but rather a relative measure of the force of resistance encountered when two surfaces of the same or different materials slide over one another. Thus, for example, the COF of a leather shoe on a freshly waxed floor can be expressed as a value, but will have no relationship to the value determined when the leather shoe is slid over a steel stair step. Thus, spherical slider 24 may be fabricated from an almost infinite number of materials depending upon the particular surface under evaluation 26 and the purpose for which the test is being performed, to achieve high resistance to sliding or low resistance to sliding. Similarly, soft materials do not necessarily "stick" or resist sliding better than harder materials.

The apparatus of the present invention finds use in innumerable applications, most particularly in the determination of the frictional characteristics encountered when an aircraft lands on an aircraft carrier deck. Thus, in this determination the surface under evaluation 26 is the surface of the aircraft carrier deck and the material of spherical slider 24 should simulate the tire of a landing aircraft.

Thus, the key criterion for the selection of the material for spherical slider 24 is that it mimic closely the frictional characteristics or frictional behavior of the material that is going to contact the surface under evaluation 26 in a particular set of circumstances or a particular application. In the case of the aircraft carrier surface previously cited, for example, neoprene is the material of choice for spherical slider 24, while in the case of the leather shoe on a stair step, a spherical leather material is appropriate for spherical slider 24. What is most important in the selection of the material for spherical slider 24 is that its use achieves good correlation between the measurements taken with frictional testing device 10 and the behavior of the surface under evaluation 26 and the contacting surface in the particular application under study.

The shape of spherical slider 24 also plays and important role in the validity of the measurements taken and their correlation with the "real world" of the particular application. It has been found that flat plates do not perform entirely satisfactorily in most applications, hence the requirement for a spherical shape for spherical slider 24. The validity or correlatablity of the results, however, also depend to some degree on the diameter of spherical slider 24. Thus, it is desirable that the ideal diameter for spherical slider 24 be determined by trial and error for a particular application.

In addition to the foregoing essential elements of frictional testing device 10, a number of other useful enhancements may be incorporated therein. These include: an angular position detector 38 to determine the relative angular location of measurement arm 22 along its circular path of travel during a friction measurement; a vertical deviation detector 40 to measure changes in height to simultaneously measure the topography of surface 26; a system lift mechanism 42 (depicted schematically in FIG. 1) to raise and lower measurement arm 22 so as to bring spherical frictional slider 24 into and out of contact with surface 26; and a load assembly 44 that can be a separate load imparting mechanism as schematically depicted in the Figures or can be incorporated as a load inducing device into yoke 30 and an associated strain gauge arrangement 46 normal to the plane of surface 26 to measure an applied load. Of course any number of alternative force detecting devices could be substituted for this strain gauge arrangement 46.

Other desirable enhancements include: a system housing 48 to protect frictional testing device 10 from environmental hazards or interferences and to provide a carrying case for device 10; a separate environmental shield located between motor 14 and measurement arm 22 to provide additional environmental protection; and a mechanism for leveling frictional testing device 10 such as the adjustable feet 52 shown in FIG. 1. Element 49 is connected to an output element from motor 14.

As is apparent to the skilled artisan, frictional testing device 10 should also include as an integral part thereof or as a separate piece of equipment with appropriate connections being provided in device 10, a data acquisition system 54 to collect, analyze and archive input from the various sensors, the tangential force detector 28, the angular position detector 38, the vertical deviation detector 46 and the load assembly 44 to accurately determine the coefficient of friction of spherical slider 24 relative to surface 26. According to a highly preferred embodiment, frictional testing device 10 also incorporates a "Go/No-Go" acceptance system 56 that provides immediate feedback to a user on the acceptability of the detected coefficient of friction of a surface under analysis as defied by predetermined frictional standards. Such a "Go/No-Go" acceptance system 56 could, for example, comprise red, yellow and green lights where green indicates acceptability, red indicates an unacceptable measurement and yellow indicates a marginal measurement.

As the invention as been described, it will be apparent to those skilled in the art that the same may be varied in many ways without departing from the spirit and scope of the invention. Any and all such modifications are intended to be included within the scope of the appended claims.

What is claimed is:

1. A device for the determination of the frictional characteristics of large surfaces comprising:
   A) a frame;
   B) a drive motor mounted in the frame;
   C) a drive train;
   D) a horizontal measurement arm having a proximate end attached to the drive train and capable of rotation about a circular path induced by the drive train and a distal end;
   E) a spherical frictional slider attached to the distal end that contacts and slides along a surface under evaluation; and
   F) a tangential force detector on the measurement arm to measure the resistance encountered by the spherical frictional slider as it slides along the surface under evaluation.

2. The device of claim 1 further including a first housing about the spherical frictional slider and engaging the spherical friction slider.

3. The device of claim 2 wherein the first housing frictionally engages the spherical friction slider.

4. The device of claim 2 further including an angular position sensor that determines the relative location of the measurement arm about the circular path.

5. The device of claim 2 further including a lift mechanism for bringing the spherical friction slider into and out of contact with the surface under evaluation.

6. The device of claim 2 further including a loading assembly that imposes a load on the measurement arm in a direction normal to the surface under evaluation.

7. The device of claim 6 further including a load force detection device to detect the amount of load applied to the measurement arm.

8. The device of claim 2 further including a vertical deviation detector on the measurement arm to detect changes in the topography of the surface under evaluation.

9. The device of claim 2 further including a second housing that contains the entire frictional testing system.

10. The device of claim 2 further including a data acquisition system for the collection, analysis and archiving of data generated by the tangential force detector.

11. The device of claim 2 further including a Go/No-Go acceptance system.

12. The device of claim 2 wherein the spherical friction slider comprises a ball.

13. A device for the determination of the frictional characteristics of large surfaces comprising:
- A) a frame;
- B) a drive motor mounted in the frame;
- C) a drive train;
- D) a horizontal measurement arm having a proximate end attached to the drive train and capable of rotation about a circular path induced by the drive train and a distal end;
- E) a spherical frictional slider attached to the distal end that contacts and slides along a surface under evaluation;
- F) a tangential force detector on the measurement arm to measure the resistance encountered by the spherical frictional slider as it slides along the surface under evaluation;
- G) a first housing about the spherical frictional slider and engaging the spherical friction slider;
- H) an angular position sensor that determines the relative location of the measurement arm about the circular path;
- I) a lift mechanism for bringing the spherical friction slider into and out of contact with the surface under evaluation;
- J) a loading assembly that imposes a load on the measurement arm in a direction normal to the surface under evaluation;
- K) a vertical deviation detector on the measurement arm to detect changes in the topography of the surface under evaluation; and
- L) a data acquisition system for the collection, analysis and archiving of data generated by the tangential force detector, the vertical deviation detector, the load detector and the angular position sensor.

14. The device of claim 13 further including a housing enclosing the device.

15. The device of claim 13 further including a Go/No-Go acceptance system.

* * * * *